United States Patent
Weast et al.

(10) Patent No.: US 9,820,513 B2
(45) Date of Patent: Nov. 21, 2017

(54) DEPTH PROXIMITY LAYERING FOR WEARABLE DEVICES

(71) Applicant: Intel Corporation, Santa Clara, CA (US)

(72) Inventors: John C. Weast, Portland, OR (US);
Wendy March, Portland, OR (US);
Eric Lewallen, Portland, OR (US);
Cory J. Booth, Beaverton, OR (US)

(73) Assignee: INTEL CORPORATION, Santa Clara, CA (US)

( * ) Notice: Subject to any disclaimer, the term of this patent is extended or adjusted under 35 U.S.C. 154(b) by 394 days.

(21) Appl. No.: 14/582,018

(22) Filed: Dec. 23, 2014

(65) Prior Publication Data

US 2016/0174620 A1    Jun. 23, 2016

(51) Int. Cl.
| | | |
|---|---|---|
| *G08B 21/00* | (2006.01) | |
| *A41D 1/00* | (2006.01) | |
| *A61B 5/00* | (2006.01) | |
| *G06F 1/16* | (2006.01) | |
| *A41B 9/00* | (2006.01) | |
| *A41B 1/08* | (2006.01) | |
| *A41D 1/02* | (2006.01) | |
| *A61B 5/01* | (2006.01) | |
| *A61B 5/024* | (2006.01) | |

(52) U.S. Cl.
CPC ............ *A41D 1/002* (2013.01); *A61B 5/0002* (2013.01); *A61B 5/6805* (2013.01); *G06F 1/163* (2013.01); *A41B 1/08* (2013.01); *A41B 9/00* (2013.01); *A41D 1/02* (2013.01); *A61B 5/01* (2013.01); *A61B 5/02444* (2013.01)

(58) Field of Classification Search
CPC .......... A41D 1/002; A61B 5/04; A61B 5/6802
USPC .......... 340/686.1, 691.1, 3.43; 600/372, 382, 600/388, 393, 509; 29/825
See application file for complete search history.

(56) References Cited

U.S. PATENT DOCUMENTS

| | | | |
|---|---|---|---|
| 8,948,839 B1 * | 2/2015 | Longinotti-Buitoni | A61B 5/6804 29/825 |
| 9,282,893 B2 * | 3/2016 | Longinotti-Buitoni | A61B 5/02055 |
| 9,330,558 B2 * | 5/2016 | Logan | A41D 1/002 |
| 2007/0091004 A1 | 4/2007 | Puuri | |
| 2009/0171180 A1 | 7/2009 | Pering et al. | |
| 2014/0045547 A1 | 2/2014 | Singamsetty et al. | |
| 2014/0184754 A1 | 7/2014 | Suh et al. | |
| 2014/0220887 A1 | 8/2014 | Yang et al. | |
| 2016/0242680 A1 * | 8/2016 | Arif | A61B 5/1112 |

OTHER PUBLICATIONS

International Search Report and Written Opinion received for PCT Patent Application No. PCT/US2015/061795, dated Mar. 8, 2016, 10 pages.

* cited by examiner

*Primary Examiner* — Toan N Pham

(57) ABSTRACT

Techniques to determine depth for a number of wearable devices, which may be worn in layers are provided. A wearable device can receive measurements from sensors to include sensors from a number of other wearable devices. Based on the sensor measurements, the wearable device can determine a depth for the wearable devices. The depth can include an indication of which wearable device is closest to a user, which wearable device is closest to an external environment, or the like.

21 Claims, 9 Drawing Sheets

DEPTH PROXIMITY LAYERING FOR WEARABLE DEVICES

BACKGROUND

Modern clothing and other wearable accessories may incorporate computing or other advanced electronic technologies. Such computing and/or advanced electronic technologies may be incorporated for various functional reasons or may be incorporated for purely aesthetic reasons. Such clothing and other wearable accessories are generally referred to as "wearable technology" or "wearable computing devices."

Wearable devices, and particularly clothing are worn in layers. For examples, on a persons torso, the following clothing may be layered: an under shirt, a t-shirt, an outershirt, and a jacket. As another example, on a persons arm, the following clothing may be layered: a watch, a long sleeve shirt, and a jacket. In each case, all these wearable items can include a sensor (e.g., to measure temperature, to measure a pulse, or the like) or other such wearable computing device. However, due to the fact that the items are layered, the readings from the sensors may differ. Conventionally, determining depth with respect to the wearable devices and determining which sensor reading is "accurate" or should be used for a particular computation or metric is not available, not intuitive, and/or difficult.

DETAILED DESCRIPTION

Figure 1:
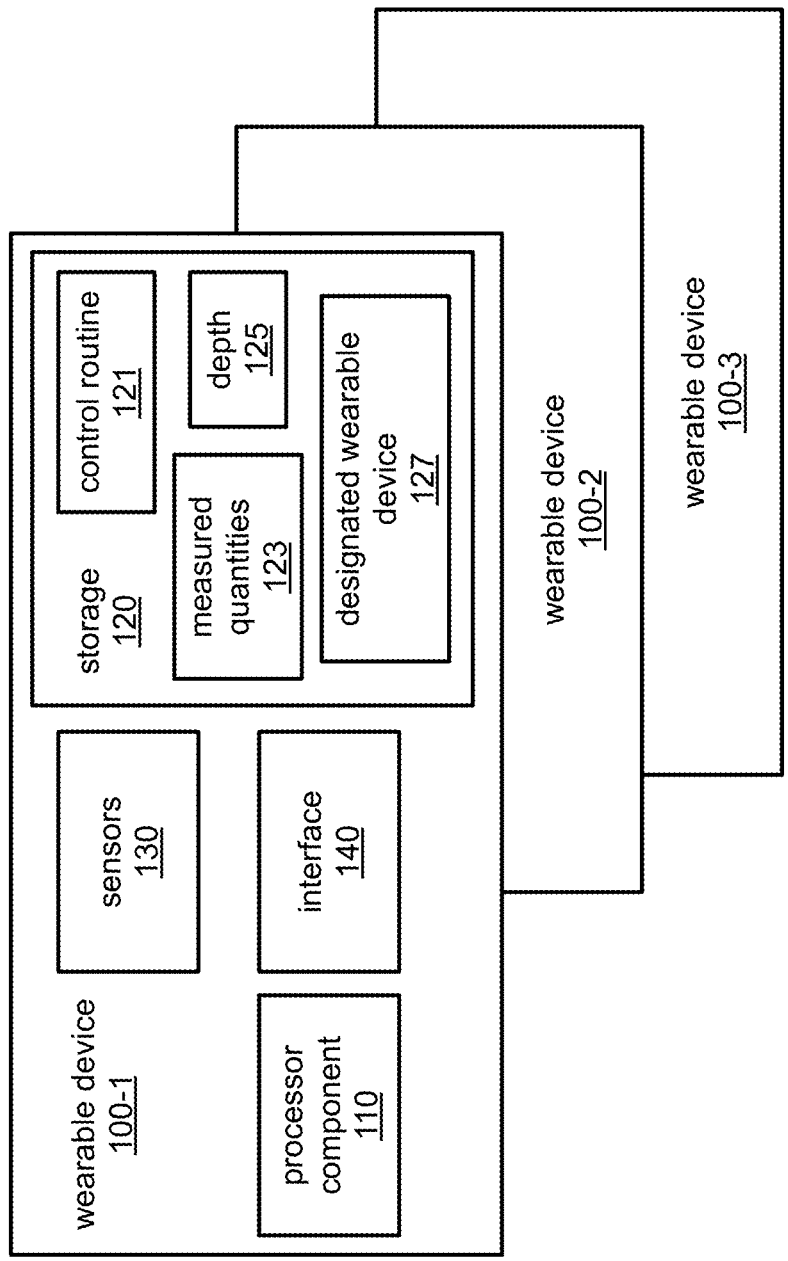
FIG. 1 is a block diagram illustrating a number of wearable devices according to at least one embodiment of the present disclosure.

Various embodiments are generally directed to a system for determining depth with respect to layered wearable devices. Said differently, the present disclosure provides a system to determine depth with respect to a number of wearable devices that may be layered. More specifically, measured quantities from a number of sensors, each associated with a different wearable device can be received. Based on the measured quantities, a depth and ordering of the wearable devices relative to each other and/or relative to a wearer can be determined. As used herein, depth can refer to an ordering of wearable devices relative to each other, or relative to a wearer. In some examples, the depth may be specified for one of the wearable devices. For example, the depth can include an indication of the wearable device closest to the wearer, farthest from the wearer, closest to the outside environment, or the like. In other examples, the depth can be specified for all the wearable devices. For example, the depth can include an indication of the ordering of the wearable devices from a specified perspective (e.g., order from the wearer, order from the outside environment, or the like).

For example, wearable devices can be incorporated into various items of removable clothing, which can be worn in layers. As a specific example, wearable devices can be incorporated into a t-shirt, a button down shirt, and a jacket. These items can be worn in layers. Each of these wearable devices may be configured to perform various functions (e.g., capture body temperature, capture ambient temperature, capture pulse, capture audio, emit sound, or the like). However, as the wearable devices are worn in layers, determining which wearable device to perform a specific function depends upon the depth or relative ordering of the wearable devices. For example, the t-shirt may be used to capture body temperature while the jacket may be used to capture ambient temperature. However, when the jacket is removed, the button down shirt may be used to capture ambient temperature.

As another example, when the jacket is worn, the jacket may be used to both capture audio and emit sound. However, when the jacket is removed, the button down shirt may be used to both capture audio and emit sound.

It is to be appreciated, that it may be intuitive to a human which wearable device should perform which function. However, the wearable devices themselves and/or a computing device operably coupled to the wearable devices do not know which device to use to perform these (or other) wearable device functions. Accordingly, the present disclosure provides wearable devices, systems, and methods for determining depth of wearable devices relative to each other and/or relative to a wearer to enable the wearable devices to designate which device to use for a particular function. In particular, the wearable devices can determine which device to use for a particular function without a user manually selecting which device is appropriate at a give time or situation. It is important to note, that the wearable devices can determine depth or other attached (e.g., via a network, via a physical connection, or the like) computing devices can determine depth. Examples are not limited in this context.

Reference is now made to the drawings, wherein like reference numerals are used to refer to like elements throughout. In the following description, for purposes of explanation, numerous specific details are set forth in order to provide a thorough understanding thereof. It may be evident, however, that the novel embodiments can be practiced without these specific details. In other instances, well known structures and devices are shown in block diagram form in order to facilitate a description thereof. The intention is to cover all modifications, equivalents, and alternatives within the scope of the claims.

FIG. 1 is a block diagram of an embodiment of a number of wearable devices 100-a, shown in a layered fashion (e.g. as may be worn as removable clothing and/or accessories). In general, one or more of the wearable devices 100-a are configured to determine depth of the wearable devices relative to each other, or relative to a user. It is important to note, that although various examples depicted herein show a limited number of wearable devices (e.g., the wearable device 100-1, 100-2, and 100-3) the present disclosure can be implemented with any number of wearable devices. However, the number of devices shown is selected for purposes of clarity of presentation and example only. Furthermore, it is worthy to note that the number of wearable devices may change during use, such as for example when a wearable device is put on or taken off by a user.

The wearable devices are configured to determine their depth relative to each other and/or a user (e.g., see FIG. 5) based on various measured quantities from sensors incorporated into the wearable devices. For example, from a general standpoint, the first wearable device 100-1 can see two other wearable devices (e.g., wearable device 100-2 and wearable device 100-3) in the same direction. The second wearable device 100-2 can see two other wearable devices (e.g., wearable device 100-1 and wearable device 100-2) but in opposite directions from each other. Likewise the wearable device 100-3 can see two other wearable devices (e.g., wearable device 100-1 and wearable device 100-2) in the same direction. Based on this, the wearable devices can determine a relative depth or ordering for each other. Furthermore, based on the measured quantities captured from sensors and the determined depth, the wearable devices can determine which wearable device to use for a particular function.

It is important to note, that with some implementations, each of the wearable devices may only "see" the adjacent wearable device. For example, the wearable device 100-1 may only see the wearable device 100-2 while the wearable device 100-2 sees both the wearable device 100-1 and 100-3. However, the present disclosure provides that readings from the sensors on the wearable devices can be used to determine a relative depth or ordering for the wearables.

Figure 2:
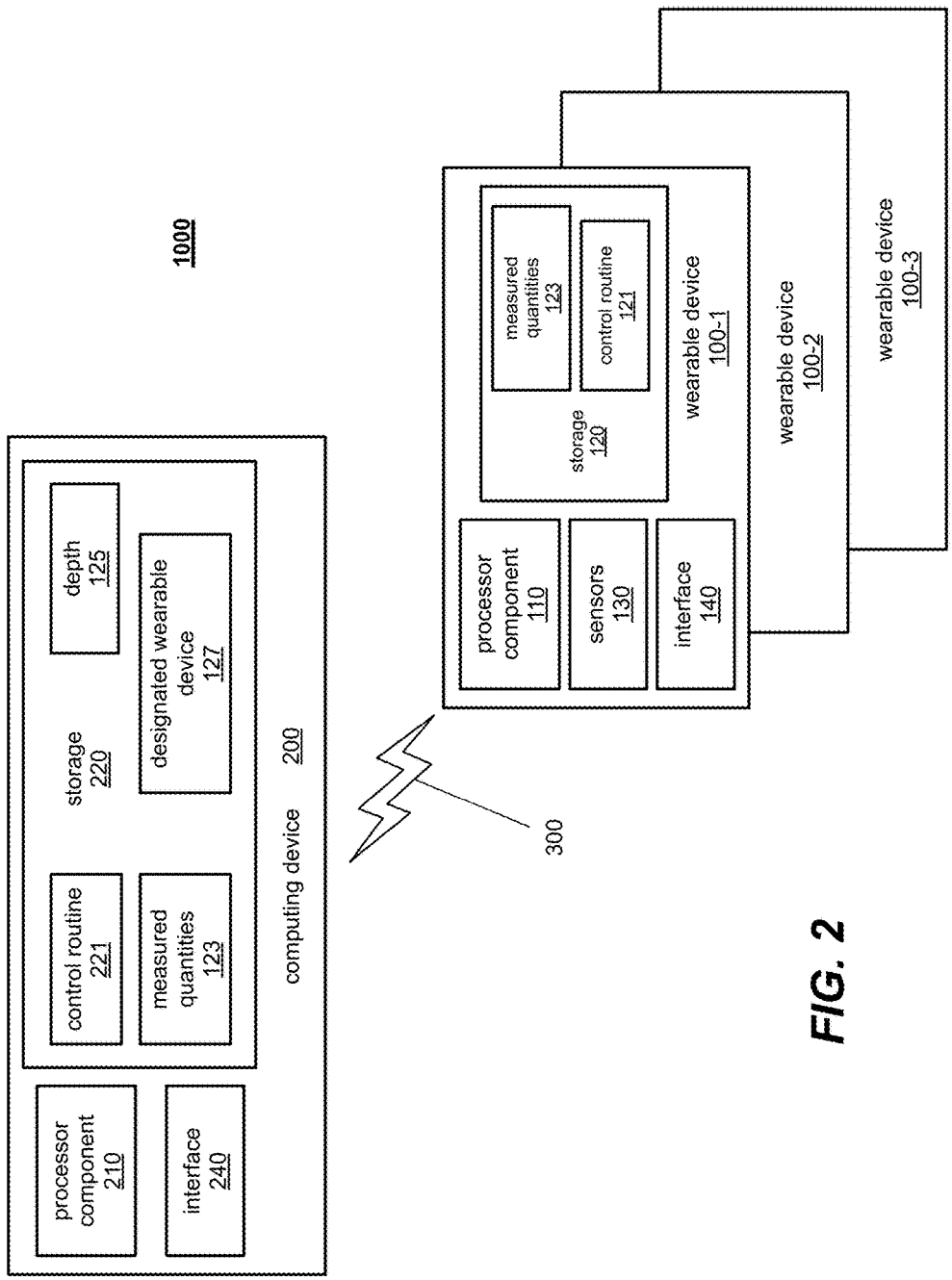
FIG. 2 is a block diagram illustrating a system for determining depth among wearable devices according to at least one embodiment of the present disclosure.

In general, each of the wearable devices may incorporate a processor component, a memory storing computer executable instructions, a sensor, and an interface to wirelessly communicate with other wearable devices and/or other computing devices (see FIG. 2). However, the wearable devices 100-1, 100-2, and 100-3 need not be identically configured and/or implemented. Furthermore, for purposes of clarity, only the wearable computing device 100-1 is referenced in describing example components of the wearable devices 100-a. It is to be appreciated however, that any of the wearable devices 100-a may be configured as described herein.

In various embodiments, the wearable computing devices 100-1 incorporates one or more of a processor component 110, storage 120, one or more sensors 130, and an interface 140. The storage 120 stores one or more of a control routine 121, measured quantities 123, a depth 125, and a designated wearable device 127. Furthermore, although not depicted in this figure, the wearable computing device 100-1 may be operably coupled to one or more other computing devices (refer to FIG. 2). For example, the wearable device 100-1 can communicate with other devices (e.g., other wearable devices, other computing devices, or the like) via a network, which may be wireless or wired. In particular, the wearable computing devices 100 may exchange signals conveying information (e.g., measured quantities, determined depth, designated devices, or the like) with other computing devices through the network.

In the wearable computing device 100-1, the control routine 121 incorporates a sequence of instructions operative on the processor component 110 in its role as a main processor component to implement logic to perform various functions. In executing the control routine 121, the processor component 110 receives an indication of a measured quantity from the sensor 130 and indications of measured quantities from the wearable devices 100-2 and/or 100-3. In particular, the processor component 110 receives indications of a portion of the measured quantities 123 from the sensor 130, which corresponds to a first wearable device (e.g., the wearable device 100-1), indications of a portion of the measured quantities 123 from a second sensor, which corresponds to a second wearable device (e.g., the wearable device 100-2), and indications of a portion of the measured quantities 123 from the a third sensor, which corresponds to a third wearable device (e.g., the wearable device 100-3).

In executing the control routine 121, the processor component 110 determines a depth with respect to the second wearable device and the third wearable device based on the measured quantities. For example, the processor component 110 can determine the depth 125 based on the measured quantities 123. In general, the measured quantities can correspond to any metric with which the sensors (e.g., the sensor 130) is configured to measure. For example, the measured quantities 123 can include an indication of a temperature, a noise level, a light level, a wireless signal strength, or an electrostatic measurement.

In some implementations, in executing the control routine 121, the processor component 110 determines whether the measured quantity corresponding to the first wearable device is greater than the measured quantity corresponding to the second wearable device and whether the measured quantity corresponding to the first wearable device is greater than the measured quantity corresponding to the third wearable device. The processor component 110 can determine the depth 125 based on based on whether the first measured quantity is greater than the second measured quantity and whether the first measured quantity is greater than the third measured quantity. Further examples of determining depth are described with respect to FIGS. 6-7.

In executing the control routine 121, the processor component 110 may also designate one of the first wearable device, the second wearable device, or the third wearable device to use for a wearable device function. Said differently, the processor component 110 may determine the designated wearable device 127, which device can be used to facilitate or perform a wearable device function (e.g., measure temperature, emit audio, capture audio, measure pulse, or the like). It is to be appreciated, that the wearable devices 110-a can be configured to perform any of a variety of different functions. Examples herein are not limited to a particular function. Furthermore, the wearable device function can include sending control signals to and/or receiving indications of output from various sensors, devices, platform components, etc., all of which are not depicted in the figures for purposes of clarity. In some examples, the sensor 130 may include a temperature sensor, microphone, a speaker, a capacitive sensor, a piezoelectric sensor, etc. The processor component 110 may receive output from the sensor 130 to include an indication of the sensor reading and store the output as the measured quantities 123. In particular, the processor component 110 may store the output from the sensor 130 as the measured quantity corresponding to the wearable device 100-1. Similarly, the processor component 110 may store the output from the sensor associated with the wearable device 100-2 as the measured quantity corresponding to the wearable device 100-2.

It is important to note, that the sensor 130 may be a sensor array, and can include any number and type of sensors. Furthermore, the wearable computing device 100-1 may be communicatively coupled to other sensors (e.g., proximity beacons, weather stations, the Internet of Things, or the like) to receive output and signals (e.g., including indications of sensor readings) from such sensor to use in determining the depth 125 and/or validating the determined depth 125. For example, in executing the control routine 121, the processor component 110 may: receive indication of a fourth measured quantity from a fourth sensor, the fourth sensor associated with the wearable device 100-1; receive indications of a fifth measured quantity from a fifth sensor, the fifth sensor associated with the wearable device 100-2; and receive indications of a sixth measured quantity from a sixth sensor, the sixth sensor associated with the wearable device 100-3. The processor component 110 can stored the fourth, fifth, and sixth measured quantities as the measured quantities 123.

In executing the control routine 121, the processor component 110 can validate the depth 125 based on the fourth measured quantity, the fifth measured quantity, and the sixth measured quantity. This is explained in greater detail below in conjunction with FIG. 7. In general, however, the processor component 110 can use multiple sensor modalities (e.g., output from microphones and piezoelectric speakers, or the like) to first determine the depth 125 and then to validate the determined depth 125.

Turning more specifically to FIG. 2, a block diagram of an embodiment of a system for determining depth among wearable devices is shown. As depicted, the system 1000 includes the wearable devices 100-*a* of FIG. 1. Additionally, the system 1000 includes a computing device 200. The computing device 200 is communicatively coupled to the wearable devices 100-*a*. In particular, the computing device 200 is communicatively coupled to the wearable device 100-1, 100-2, and 100-3 via the network 300. In particular, the wearable computing devices 100-1, 100-2, and 100-3 may exchange signals conveying information (e.g., measured quantities, determined depth, designated devices, or the like) with the computing device 200 through the network 300.

In general, the computing device 200 can be configured to determine depth for the wearable devices 100-1, 100-2, and 100-3. For example, with some embodiments, ones of the wearable devices may be processing and/or memory constrained. As such, the computing device 200 may be used to determine depth.

In some examples, the computing device 200 can be a device to which the wearable device 100-1, 100-2, and 100-3 sync. For example, the computing device 200 can be a smartphone, a tablet computer, a laptop computer, a cloud based synchronization system, or the like. Furthermore, in some examples, the computing device 200 can itself be incorporated into a wearable device.

In general, the computing device 200 is configured to determine a depth of the wearable devices 100-1, 100-2, and 100-3 relative to each other, or relative to a user. In various embodiments, the computing device 200 incorporates one or more of a processor component 210, storage 220, and an interface 240. The storage 220 stores one or more of a control routine 221, measured quantities 123, a depth 125, and a designated wearable device 127.

In the computing device 200, the control routine 221 incorporates a sequence of instructions operative on the processor component 210 in its role as a main processor component to implement logic to perform various functions. In executing the control routine 221, the processor component 210 receives an indication of measured quantities from the wearable computing devices 100-1, 100-2, and 100-3. For example, the processor component 210 receives an indication of a portion of the measured quantities 123 (e.g., one or more of, or the like) from the sensor 130 of the wearable device 100-1.

In executing the control routine 221, the processor component 210 determines a depth of the wearable devices 100-1, 100-2, and 100-3 relative to each other, relative to a wearer, and/or relative to an external environment. For example, the processor component 210 can determine the depth 125 based on the measured quantities 123. As noted above, the measured quantities 123 can correspond to any metric with which the sensors (e.g., the sensor 130) are configured to measure. For example, the measured quantities 123 can include an indication of a temperature, a noise level, a light level, a wireless signal strength, or an electrostatic measurement.

In some implementations, in executing the control routine 221, the processor component 210 determines whether the measured quantity corresponding to the first wearable device (e.g., the wearable device 100-1) is greater than the measured quantity corresponding to the second wearable device (e.g., the wearable device 100-2) and whether the measured quantity corresponding to the first wearable device is greater than the measured quantity corresponding to the third wearable device (e.g., the wearable device 100-3). The processor component 210 can determine the depth 125 based on based on whether the first measured quantity is greater than the second measured quantity and whether the first measured quantity is greater than the third measured quantity. Further examples of determining depth are described with respect to FIGS. 6-7.

In executing the control routine 221, the processor component 210 may also designate one of the first wearable device, the second wearable device, or the third wearable device to use for a wearable device function. Said differently, the processor component 210 may determine the designated wearable device 127, which device can be used to facilitate or perform a wearable device function (e.g., measure temperature, emit audio, capture audio, measure pulse, or the like). It is to be appreciated, that the wearable devices 100-1, 100-2, and 100-3 can be configured to perform any of a variety of different functions. Examples herein are not limited to a particular function. Furthermore, the wearable device function can include sending control signals to and/or receiving indications of output from various sensors, devices, platform components, etc., all of which are not depicted in the figures for purposes of clarity. For example, as noted, the sensor 130 may include a temperature sensor, microphone, a speaker, a capacitive sensor, a piezoelectric sensor, etc. The processor component 210 may receive output from the sensor 230 to include an indication of the sensor reading and store the output as the measured quantities 123. In particular, the processor component 210 may store the output from the sensor 130 as the measured quantity corresponding to the wearable device 100-1. Similarly, the processor component 210 may store the output from the sensor associated with the wearable device 100-2 as the measured quantity corresponding to the wearable device 100-2.

It is important to note, that the sensor 130 may be a sensor array, and can include any number and type of sensors. Furthermore, the wearable computing device 100-1 may be communicatively coupled to other sensors (e.g., proximity beacons, weather stations, the Internet of Things, or the like) to receive output and signals (e.g., including indications of sensor readings) from such sensor to use in determining the depth 125 and/or validating the determined depth 125. For example, in executing the control routine 221, the processor component 210 may: receive indication of a fourth measured quantity from a fourth sensor, the fourth sensor associated with the wearable device 100-1; receive indications of a fifth measured quantity from a fifth sensor, the fifth sensor associated with the wearable device 100-2; and receive indications of a sixth measured quantity from a sixth sensor, the sixth sensor associated with the wearable device 100-3.

The processor component 110 can stored the fourth, fifth, and sixth measured quantities as the measured quantities 123.

In executing the control routine 221, the processor component 210 can validate the depth 125 based on the fourth measured quantity, the fifth measured quantity, and the sixth measured quantity. This is explained in greater detail below in conjunction with FIG. 7. In general, however, the processor component 210 can use multiple sensor modalities (e.g., output from microphones and piezoelectric speakers, or the like) to first determine the depth 125 and then to validate the determined depth 125.

In various embodiments, the processor component 110 and/or the processor components 210 may include any of a wide variety of commercially available processors. Further, one or more of these processor components may include multiple processors, a multi-threaded processor, a multi-core processor (whether the multiple cores coexist on the same or separate dies), and/or a multi-processor architecture of some other variety by which multiple physically separate processors are in some way linked.

In various embodiments, the storage 120 and/or 220 may be based on any of a wide variety of information storage technologies, possibly including volatile technologies requiring the uninterrupted provision of electric power, and possibly including technologies entailing the use of machine-readable storage media that may or may not be removable. Thus, each of these storages may include any of a wide variety of types (or combination of types) of storage device, including without limitation, read-only memory (ROM), random-access memory (RAM), dynamic RAM (DRAM), Double-Data-Rate DRAM (DDR-DRAM), synchronous DRAM (SDRAM), static RAM (SRAM), programmable ROM (PROM), erasable programmable ROM (EPROM), electrically erasable programmable ROM (EEPROM), flash memory, polymer memory (e.g., ferroelectric polymer memory), ovonic memory, phase change or ferroelectric memory, silicon-oxide-nitride-oxide-silicon (SONOS) memory, magnetic or optical cards, one or more individual ferromagnetic disk drives, or a plurality of storage devices organized into one or more arrays (e.g., multiple ferromagnetic disk drives organized into a Redundant Array of Independent Disks array, or RAID array). It should be noted that although each of these storages is depicted as a single block, one or more of these may include multiple storage devices that may be based on differing storage technologies. Thus, for example, one or more of each of these depicted storages may represent a combination of an optical drive or flash memory card reader by which programs and/or data may be stored and conveyed on some form of machine-readable storage media, a ferromagnetic disk drive to store programs and/or data locally for a relatively extended period, and one or more volatile solid state memory devices enabling relatively quick access to programs and/or data (e.g., SRAM or DRAM). It should also be noted that each of these storages may be made up of multiple storage components based on identical storage technology, but which may be maintained separately as a result of specialization in use (e.g., some DRAM devices employed as a main storage while other DRAM devices employed as a distinct frame buffer of a graphics controller).

In various examples, the sensors 130 may include one or more sensors, such as, for example, a temperature sensor, a speaker, a light sensor, an accelerometer, a microphone, a gyroscope, a GPS sensor, a magnetic sensor, a piezoelectric sensor, a capacitive sensor, a biometric sensor, or the like. It is important to note, that the wearable devices 100-*a* can be implemented to measure any of a variety of metrics using the sensors. As such, examples are not limited to those given here.

In various embodiments, the interface 140 and/or 240 may employ any of a wide variety of signaling technologies enabling computing devices to be coupled to other devices as has been described. Each of these interfaces may include circuitry providing at least some of the requisite functionality to enable such coupling. However, each of these interfaces may also be at least partially implemented with sequences of instructions executed by corresponding ones of the processor components (e.g., to implement a protocol stack or other features). Where electrically and/or optically conductive cabling is employed, these interfaces may employ signaling and/or protocols conforming to any of a variety of industry standards, including without limitation, RS-232C, RS-422, USB, Ethernet (IEEE-802.3) or IEEE-1394. Where the use of wireless signal transmission is entailed, these interfaces may employ signaling and/or protocols conforming to any of a variety of industry standards, including without limitation, IEEE 802.11a, 802.11b, 802.11g, 802.11n, 802.16, 802.20 (commonly referred to as "Mobile Broadband Wireless Access"); Bluetooth; ZigBee; or a cellular radiotelephone service such as GSM with General Packet Radio Service (GSM/GPRS), CDMA/1× RTT, Enhanced Data Rates for Global Evolution (EDGE), Evolution Data Only/Optimized (EV-DO), Evolution For Data and Voice (EV-DV), High Speed Downlink Packet Access (HSDPA), High Speed Uplink Packet Access (HSUPA), 4G LTE, etc.

Figure 3:
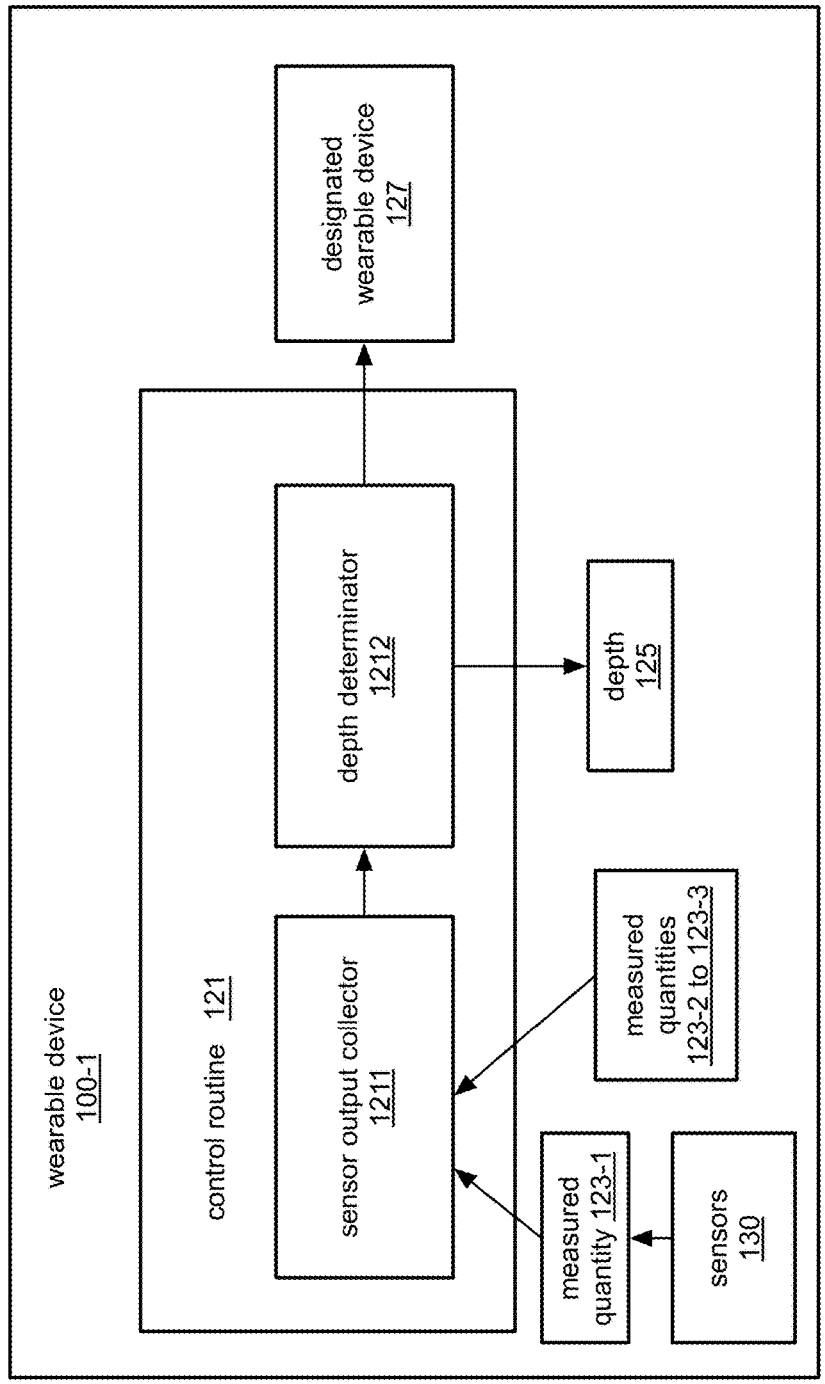
FIGS. 3-4 illustrate examples of portions of the wearable device and system of FIGS. 1-2.
Figure 4:
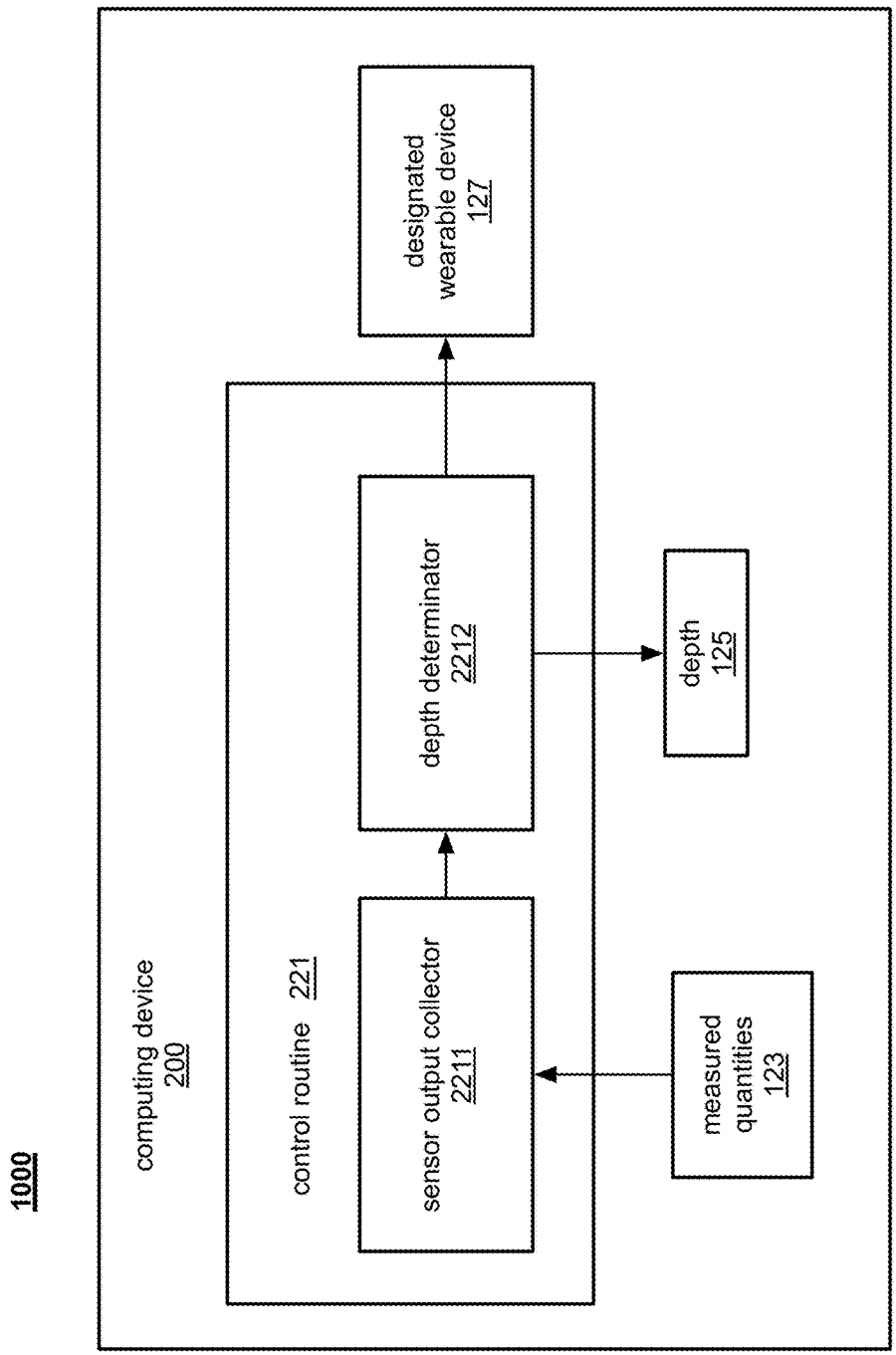

FIGS. 3-4 are block diagrams of portions of an embodiment of the wearable computing device 100-1 and the computing device 200 of the system 1000 of FIG. 1-2. In general, FIG. 3 illustrates aspects of the operation of the wearable computing device 100-1 while FIG. 4 illustrates aspects of the operation of the computing device 200 of the system 1000. In various embodiments, the control routines 121 and/or 221 may include one or more of an operating system, device drivers and/or application-level routines (e.g., so-called "software suites" provided on disc media, "applets" obtained from a remote server, or the like). Where an operating system is included, the operating system may be any of a variety of available operating systems appropriate for whatever corresponding ones of the processor component 110 and/or 210. Where one or more device drivers are included, those device drivers may provide support for any of a variety of other components, whether hardware or software components, of the wearable device 100-1 and/or the computing device 200.

Turning more specifically to FIG. 3, the control routine 121 includes a sensor output collector 1211 and a depth determinator 1212. It is important note that is some examples the determination of depth can be performed on another computing device (refer to FIG. 4).

In general, the control routine 121 causes the wearable computing device 100-1 to receive output from sensors (including the sensor 130 as well as sensor associated with other wearable computing devices) to include indications of the measured quantities 123. The control routine additionally determines the depth 125 and optionally the designated wearable device 127 based on the measured quantities.

In particular, the sensor output collector 1211 receives output from the sensors 130. More specifically, the sensor output collector 1211 receives the measured quantity corresponding to a first wearable device (e.g., the wearable device 100-1). Additionally, the sensor output collector 1211 receives the measured quantities corresponding to a number of other wearable devices (e.g., the wearable device 100-2, the wearable device 100-3, etc.). The sensor output collector 1211 can store the received output as the measured quantities 123.

The depth determinator 1212 determines the depth based on the measured quantities. In particular, the depth determinator 1212 determines the depth 125 based on the measured quantities 123. For example, the depth determinator 1212 can determine a layer ordering for the wearable devices 100-1, 100-2, and 100-3. As another example, the depth determinator 1212 can determine a one of the wearable devices closest to the wearer, closest to the external environment, or the like.

It is important to note, the depth determinator 1212 can determine a depth for the wearable device 100-1, 100-2, and/or 100-3 that is relative to another wearable device. For example, the depth determiantor 1212 can determine that the wearable device 100-1 is closer to a user than the wearable device 100-2. However, the depth determiantor 1212 may not necessarily determine an absolute depth (e.g., overall depth for each device relative to a fixed point).

Furthermore, the depth determinator 1212 can determine a one of the wearable devices 100-a to perform a wearable device function based on the depth. For example, the depth determinator 1212 can determine the depth 125 to include an indication that the wearable device 100-1 is closest to an external environment and determine the designated wearable device 127 to include an indication that the wearable device 100-1 is to measure ambient temperature.

Turning more specifically to FIG. 4, the control routine 221 includes a sensor output collector 2211 and a depth determinator 2212. In general, the control routine 221 causes the computing device 200 to receive output from sensors associated with a number of wearable computing devices. In particular, the sensor output collector 2211 can receive output from the sensors associated with the wearable computing devices 100-1, 100-2, and 100-3, the output to include indications of the measured quantities 123. The control routine 221 additionally determines the depth 125 and optionally the designated wearable device 127 based on the measured quantities.

In particular, the sensor output collector 2211 receives the measured quantity corresponding to a first wearable device (e.g., the wearable device 100-1), the measured quantities corresponding to a second wearable device (e.g., the wearable device 100-2), and a third wearable device (e.g., the wearable device 100-3). The sensor output collector 2211 can receive the output directly from the sensor and store the received output as the measured quantities 123. In some examples, the sensor output collector 2211 can receive the measured quantities 123 directly.

The depth determinator 2212 determines the depth based on the measured quantities. In particular, the depth determinator 2212 determines the depth 125 based on the measured quantities 123. For example, the depth determinator 2212 can determine an layer ordering for the wearable devices 100-1, 100-2, and 100-3. As another example, the depth determinator 2212 can determine a one of the wearable devices closest to the wearer, closest to the external environment, or the like.

Furthermore, the depth determinator 2212 can determine a one of the wearable devices 100-a to perform a wearable device function based on the depth. For example, the depth determinator 2212 can determine the depth 125 to include an indication that the wearable device 100-1 is closest to an external environment and determine the designated wearable device 127 to include an indication that the wearable device 100-1 is to measure ambient temperature.

Figure 5:
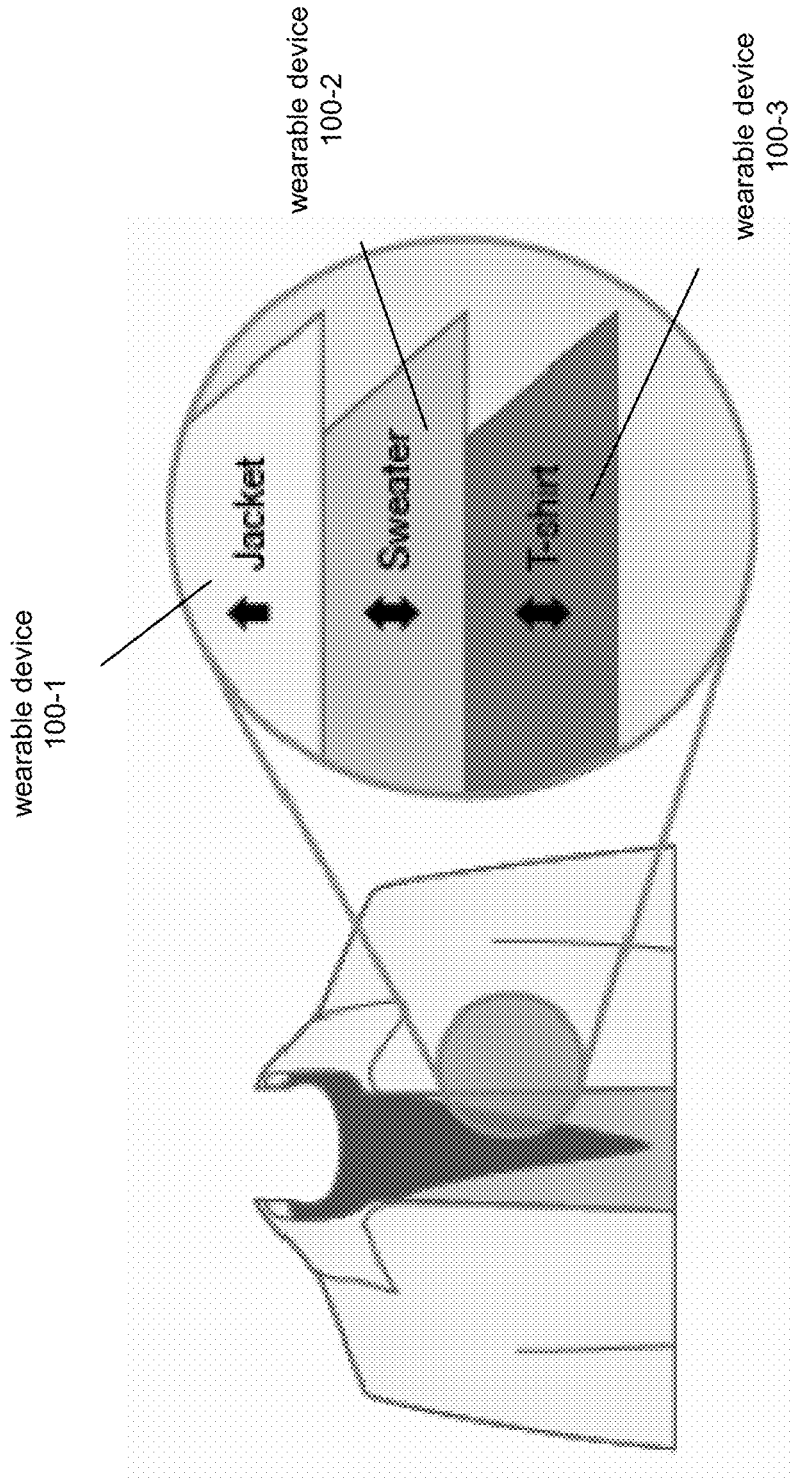
FIG. 5 is an illustration of a number of wearable devices worn in a layered fashion that may implement to wearable device or the system of FIGS. 1-2.

FIG. 5 illustrates the wearable devices 100-1, 100-2, and 100-3 of FIGS. 1-4 implemented as removable clothing. In particular, as depicted, the wearable device 100-1 is implemented in a jacket, the wearable device 100-2 is implemented in a sweater, and the wearable device 100-3 is implemented in a t-shirt. Furthermore, the wearable devices 100-1, 100-2, and 100-3 are shown worn in layers. More specifically, the t-shirt (e.g., wearable device 100-3) is depicted worn on a layer closest to the wearer or farthest from the external environment. The sweater (e.g., wearable device 100-2) is depicted worn in a middle layer or between the t-shirt and jacket. The jacket (e.g., the wearable device 100-1) is depicted worn on an external layer or closest to the external environment or farthest from the users skin. It is to be appreciated, that the wearable computing devices 100-1, 100-2, and 100-3 can be incorporated into any of a variety of different types of wearable devices. Providing an exhaustive list is not feasible. As such, examples herein are provided for purposes of clarity of explanation and not to be limiting.

Figure 6:
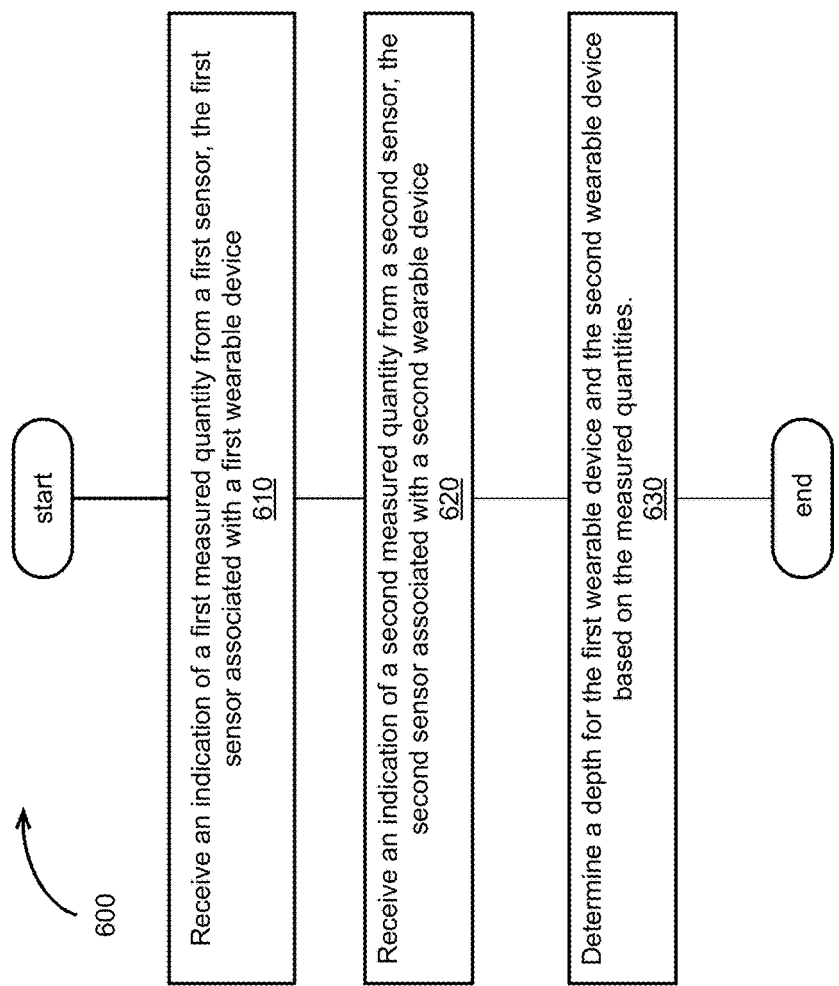
FIGS. 6-7 illustrate examples of logic flows according to embodiments.
Figure 7:
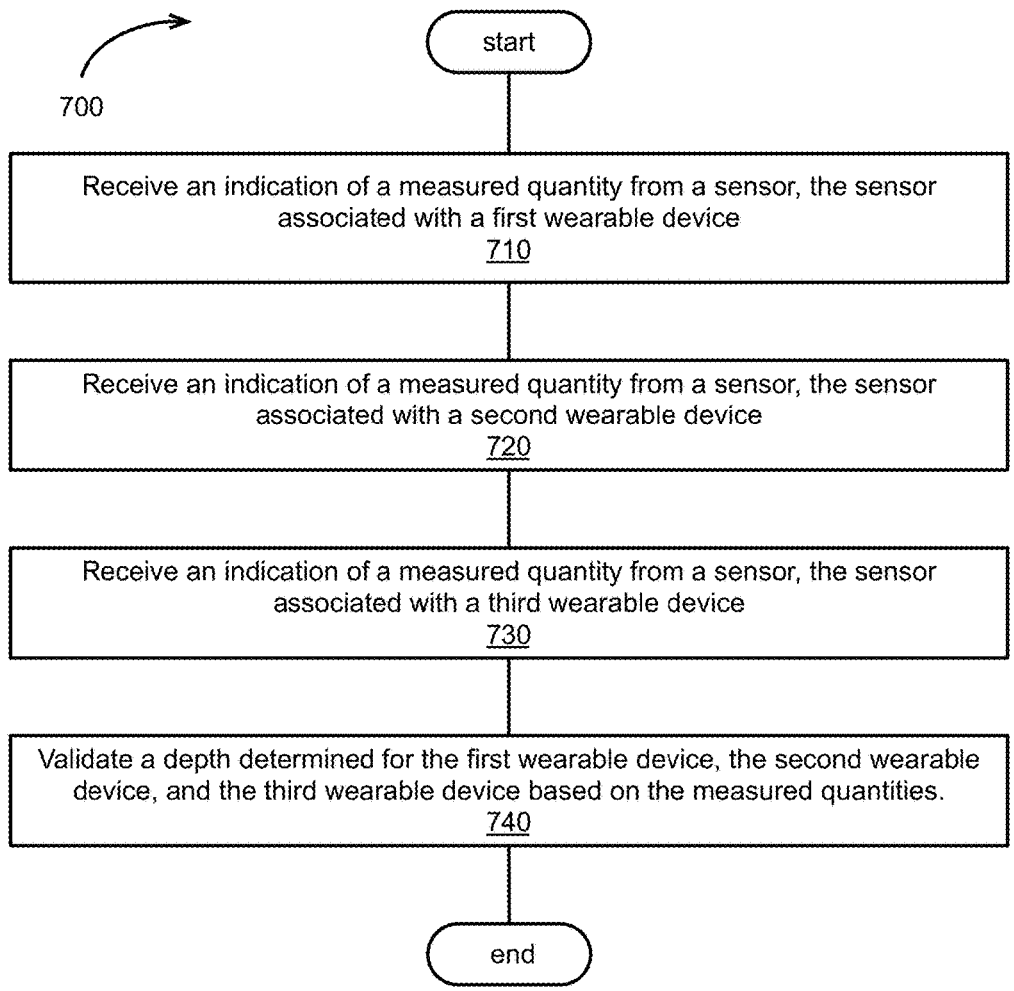

FIGS. 6-7 illustrate example embodiments of logic flows that may be implement by the wearable devices 100-a and/or the computing device 200. The illustrated logic flows may be representative of some or all of the operations executed by one or more embodiments described herein. More specifically, the logic flows may illustrate operations performed by the processor components 110 and/or the 220 in executing at least the control routines 121 and/or 221. Although the logic flows are described with reference to FIGS. 1-5, examples are not limited in this context. In particular, the example implementation as a t-shirt, sweater, and jacket shown in FIG. 5 are used to provide various examples of determining depth. However, this is not intended to be limiting.

Turning more specifically to FIG. 6, a logic flow 600 is depicted. The logic flow 600 may begin at block 610. At block 610, a processor component (e.g., the processor component 110 of the wearable device 100-1, the processor component 210 of the computing device 200, or the like) receives a first measured quantity from a first sensor associated with a first wearable device. For example, the processor component can receive a measured quantity from the sensor 130 of the wearable device 100-1.

Continuing to block 620, the processor component receives a second measured quantity from a second sensor associated with a second wearable device. For example, the processor component can receive a measured quantity from a sensor of the wearable device 100-2.

Continuing to block 630, the processor component determines a depth for the first wearable device and the second wearable device. For example, the processor component can determine the wearable device 100-1 is closer to the wearer than the wearable device 100-2. It is to be appreciated that the logic flow 600 can receive measured quantities associated with a number of wearable devices. Furthermore, the logic flow 600 can be repeatedly performed to determine depth of wearable devices at different times during use. In particular, the logic flow 600 can be performed repeatedly to determine a depth when a first number of wearable devices are worn in a layered fashion (e.g., the jacket, sweater, and t-shirt of FIG. 5) and when a second number of wearable devices are worn in a layered fashion (e.g., the t-shirt and sweater of FIG. 5).

For example, at block 610 and 620, the processor component can receive an indication of a capacitive or other signal transmitted through the body received by sensors on the wearable devices 100-1, 110-2, and 100-3. At block 630, the processor component can determine a depth for the devices based on the received signal. For example, the stronger the received signal, the closer the corresponding wearable device is to the body.

As another example, at block 610 and 620, the processor component can receive an indication of a temperature measured by sensors on the wearable devices 100-1, 110-2, and 100-3. At block 630, the processor component can determine a depth for the devices based on the measured temperature. For example, the closer the measured temperature is to 98.6, the closer the corresponding wearable device is to the body.

As another example, at block 610 and 620, the processor component can receive an indication of a light measured by sensors on the wearable devices 100-1, 110-2, and 100-3. At block 630, the processor component can determine a depth for the devices based on the measured light. For example, the relative presence or absence of light can be used to determine the depth of the wearable devices.

As another example, at block 610 and 620, the processor component can receive an indication of an ambient noise level measured by sensors on the wearable devices 100-1, 110-2, and 100-3. At block 630, the processor component can determine a depth for the devices based on the ambient noise level. For example, the higher the ambient noise level the closer to the external layer the corresponding wearable device is.

Turning more specifically to FIG. 7, a logic flow 700 is depicted. In general, the logic flow 700 can validate a determined depth based on additional sensor readings, which may be from alternative sensor modalities. Logic flow 700 may be begin at block 710. At block 710, a processor component (e.g., the processor component 110 of the wearable device 100-1, the processor component 210 of the computing device 200, or the like) receives a measured quantity from a sensor associated with a first wearable device. For example, the processor component can receive a measured quantity from the sensor 130 of the wearable device 100-1.

Continuing to block 720, the processor component receives a measured quantity from a sensor associated with a second wearable device. For example, the processor component can receive a measured quantity from a sensor of the wearable device 100-2.

Continuing to block 730, the processor component receives a measured quantity from a sensor associated with a third wearable device. For example, the processor component can receive a measured quantity from a sensor of the wearable device 100-3.

Continuing to block 740, the processor component validates a depth determined for the first, second, and third wearable device based on the measured quantities. For example, the depth 125 can be determined (e.g., refer to FIG. 6) based on ambient noise levels measured buy microphones on each of the wearable devices 100-1, 100-2, and 100-3. At blocks 710, 720, and 730, a piezoelectric speaker (e.g., on one of the wearable devices, or the like) can vibrate at a specific frequency (e.g., 20,000 Hz) and the microphones can measure the sound. The slight difference in sound between the layered wearable devices may be evident and can be used (e.g., at block 740) to validate the determined depth.

Figure 8:
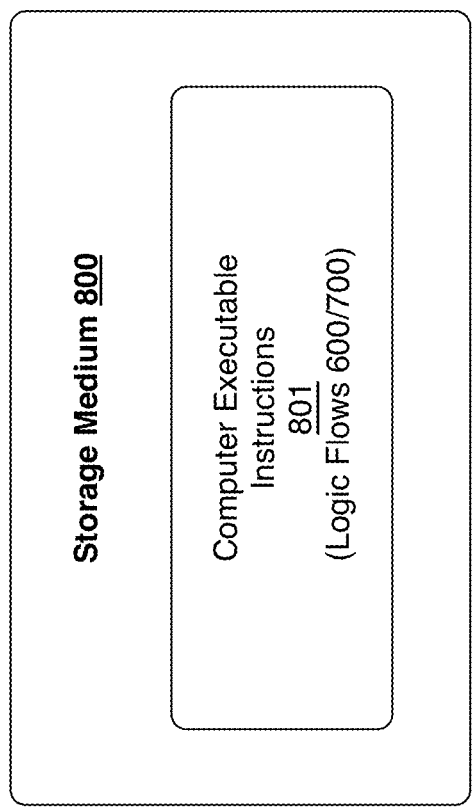
FIG. 8 illustrates a storage medium according to an embodiment.

FIG. 8 illustrates an embodiment of a storage medium 800. The storage medium 800 may comprise an article of manufacture. In some examples, the storage medium 800 may include any non-transitory computer readable medium or machine readable medium, such as an optical, magnetic or semiconductor storage. The storage medium 800 may store various types of computer executable instructions 801, such as instructions to implement logic flows 600, and/or 700. Examples of a computer readable or machine readable storage medium may include any tangible media capable of storing electronic data, including volatile memory or non-volatile memory, removable or non-removable memory, erasable or non-erasable memory, writeable or re-writeable memory, and so forth. Examples of computer executable instructions may include any suitable type of code, such as source code, compiled code, interpreted code, executable code, static code, dynamic code, object-oriented code, visual code, and the like. The examples are not limited in this context.

Figure 9:
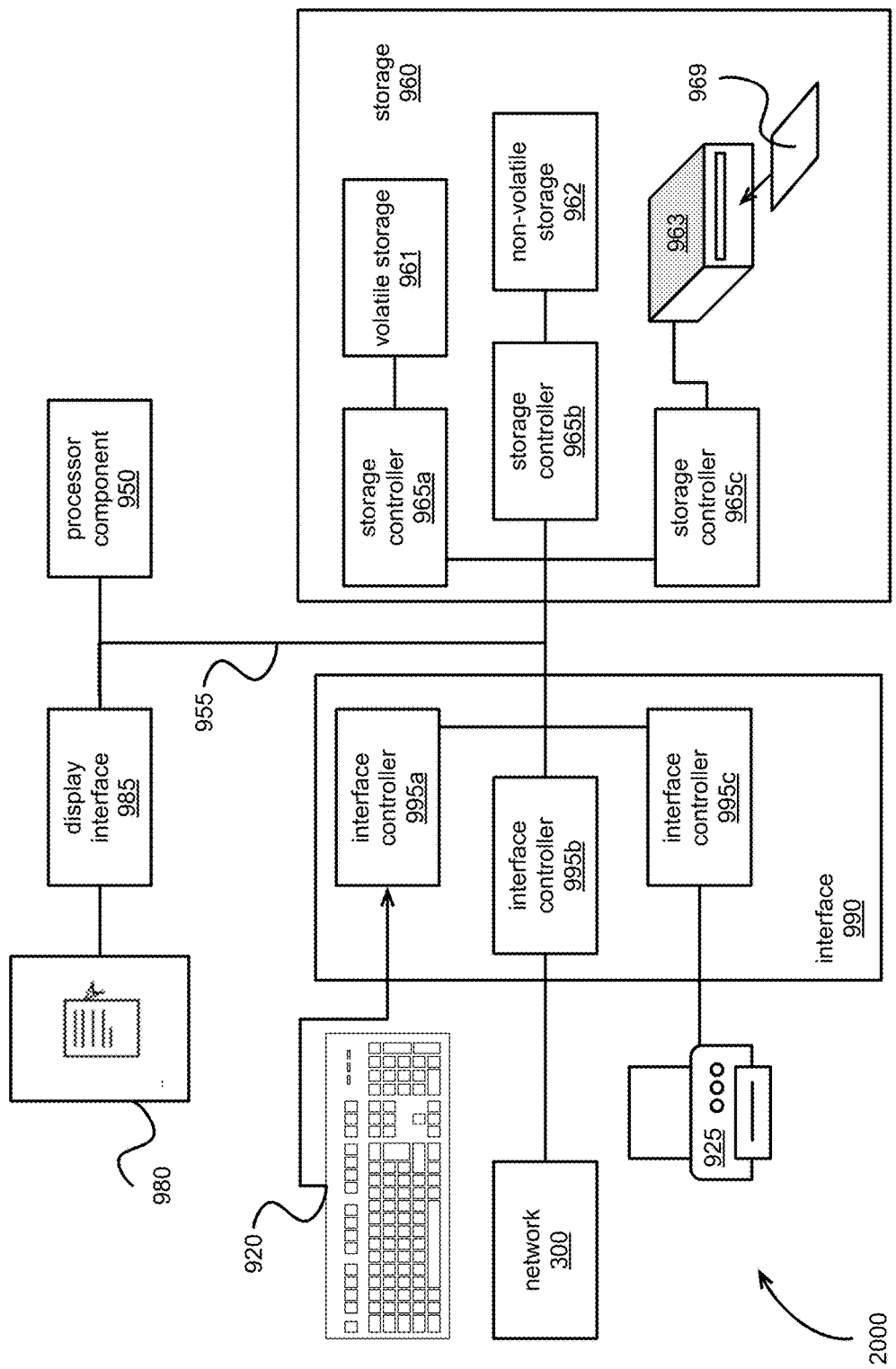
FIG. 9 illustrates a processing architecture according to an embodiment.

FIG. 9 illustrates an embodiment of an exemplary processing architecture 2000 suitable for implementing various embodiments as previously described. More specifically, the processing architecture 2000 (or variants thereof) may be implemented as part of the wearable computing devices 100-1, 100-2, 100-3, and/or the system 1000.

The processing architecture 2000 may include various elements commonly employed in digital processing, including without limitation, one or more processors, multi-core processors, co-processors, memory units, chipsets, controllers, peripherals, interfaces, oscillators, timing devices, video cards, audio cards, multimedia input/output (I/O) components, power supplies, etc. As used in this application, the terms "system" and "component" are intended to refer to an entity of a computing device in which digital processing is carried out, that entity being hardware, a combination of hardware and software, software, or software in execution, examples of which are provided by this depicted exemplary processing architecture. For example, a component can be, but is not limited to being, a process running on a processor component, the processor component itself, a storage device (e.g., a hard disk drive, multiple storage drives in an array, etc.) that may employ an optical and/or magnetic storage medium, an software object, an executable sequence of instructions, a thread of execution, a program, and/or an entire computing device (e.g., an entire computer). By way of illustration, both an application running on a server and the server can be a component. One or more components can reside within a process and/or thread of execution, and a component can be localized on one computing device and/or distributed between two or more computing devices. Further, components may be communicatively coupled to each other by various types of communications media to coordinate operations. The coordination may involve the uni-directional or bi-directional exchange of information. For instance, the components may communicate information in the form of signals communicated over the communications media. The information can be implemented as signals allocated to one or more signal lines. A message (including a command, status, address or data message) may be one of such signals or may be a plurality of such signals, and may be transmitted either serially or substantially in parallel through any of a variety of connections and/or interfaces.

As depicted, in implementing the processing architecture 2000, a computing device may include at least a processor component 950, a storage 960, an interface 990 to other devices, and a coupling 955. As will be explained, depending on various aspects of a computing device implementing the processing architecture 2000, including its intended use and/or conditions of use, such a computing device may further include additional components, such as without limitation, a display interface 985.

The coupling 955 may include one or more buses, point-to-point interconnects, transceivers, buffers, crosspoint switches, and/or other conductors and/or logic that communicatively couples at least the processor component 950 to the storage 960. Coupling 955 may further couple the processor component 950 to one or more of the interface 990, the audio subsystem 970 and the display interface 985 (depending on which of these and/or other components are also present). With the processor component 950 being so coupled by couplings 955, the processor component 950 is able to perform the various ones of the tasks described at length, above, for whichever one(s) of the aforedescribed computing devices implement the processing architecture 2000. Coupling 955 may be implemented with any of a variety of technologies or combinations of technologies by which signals are optically and/or electrically conveyed. Further, at least portions of couplings 955 may employ timings and/or protocols conforming to any of a wide variety of industry standards, including without limitation, Accelerated Graphics Port (AGP), CardBus, Extended Industry Standard Architecture (E-ISA), Micro Channel Architecture (MCA), NuBus, Peripheral Component Interconnect (Extended) (PCI-X), PCI Express (PCI-E), Personal Computer Memory Card International Association (PCMCIA) bus, HyperTransport™, QuickPath, and the like.

As previously discussed, the processor component 950 (corresponding to the processor component 110 and/or 210) may include any of a wide variety of commercially available processors, employing any of a wide variety of technologies and implemented with one or more cores physically combined in any of a number of ways.

As previously discussed, the storage 960 (corresponding to the storage 130 and/or 230) may be made up of one or more distinct storage devices based on any of a wide variety of technologies or combinations of technologies. More specifically, as depicted, the storage 960 may include one or more of a volatile storage 961 (e.g., solid state storage based on one or more forms of RAM technology), a non-volatile storage 962 (e.g., solid state, ferromagnetic or other storage not requiring a constant provision of electric power to preserve their contents), and a removable media storage 963 (e.g., removable disc or solid state memory card storage by which information may be conveyed between computing devices). This depiction of the storage 960 as possibly including multiple distinct types of storage is in recognition of the commonplace use of more than one type of storage device in computing devices in which one type provides relatively rapid reading and writing capabilities enabling more rapid manipulation of data by the processor component 950 (but possibly using a "volatile" technology constantly requiring electric power) while another type provides relatively high density of non-volatile storage (but likely provides relatively slow reading and writing capabilities).

Given the often different characteristics of different storage devices employing different technologies, it is also commonplace for such different storage devices to be coupled to other portions of a computing device through different storage controllers coupled to their differing storage devices through different interfaces. By way of example, where the volatile storage 961 is present and is based on RAM technology, the volatile storage 961 may be communicatively coupled to coupling 955 through a storage controller 965a providing an appropriate interface to the volatile storage 961 that perhaps employs row and column addressing, and where the storage controller 965a may perform row refreshing and/or other maintenance tasks to aid in preserving information stored within the volatile storage 961. By way of another example, where the non-volatile storage 962 is present and includes one or more ferromagnetic and/or solid-state disk drives, the non-volatile storage 962 may be communicatively coupled to coupling 955 through a storage controller 965b providing an appropriate interface to the non-volatile storage 962 that perhaps employs addressing of blocks of information and/or of cylinders and sectors. By way of still another example, where the removable media storage 963 is present and includes one or more optical and/or solid-state disk drives employing one or more pieces of machine-readable storage medium 969, the removable media storage 963 may be communicatively coupled to coupling 955 through a storage controller 965c providing an appropriate interface to the removable media storage 963 that perhaps employs addressing of blocks of information, and where the storage controller 965c may coordinate read, erase and write operations in a manner specific to extending the lifespan of the machine-readable storage medium 969.

One or the other of the volatile storage 961 or the non-volatile storage 962 may include an article of manufacture in the form of a machine-readable storage media on which a routine including a sequence of instructions executable by the processor component 950 to implement various embodiments may be stored, depending on the technologies on which each is based. By way of example, where the non-volatile storage 962 includes ferromagnetic-based disk drives (e.g., so-called "hard drives"), each such disk drive typically employs one or more rotating platters on which a coating of magnetically responsive particles is deposited and magnetically oriented in various patterns to store information, such as a sequence of instructions, in a manner akin to storage medium such as a floppy diskette. By way of another example, the non-volatile storage 962 may be made up of banks of solid-state storage devices to store information, such as sequences of instructions, in a manner akin to a compact flash card. Again, it is commonplace to employ differing types of storage devices in a computing device at different times to store executable routines and/or data. Thus, a routine including a sequence of instructions to be executed by the processor component 950 to implement various embodiments may initially be stored on the machine-readable storage medium 969, and the removable media storage 963 may be subsequently employed in copying that routine to the non-volatile storage 962 for longer term storage not requiring the continuing presence of the machine-readable storage medium 969 and/or the volatile storage 961 to enable more rapid access by the processor component 950 as that routine is executed.

As previously discussed, the interface 990 (corresponding to the interface 160 and/or 260) may employ any of a variety of signaling technologies corresponding to any of a variety of communications technologies that may be employed to communicatively couple a computing device to one or more other devices. Again, one or both of various forms of wired or wireless signaling may be employed to enable the processor component 950 to interact with input/output devices (e.g., the depicted example keyboard 920 or printer 925) and/or other computing devices, possibly through a network or an interconnected set of networks. In recognition of the often greatly different character of multiple types of signaling and/or protocols that must often be supported by any one computing device, the interface 990 is depicted as including multiple different interface controllers 995a, 995b and 995c. The interface controller 995a may employ any of a variety of types of wired digital serial interface or radio frequency wireless interface to receive serially transmitted messages from user input devices, such as the depicted keyboard 920.

The interface controller 995b may employ any of a variety of cabling-based or wireless signaling, timings and/or protocols to access other computing devices through the depicted network 300 (perhaps a network made up of one or more links, smaller networks, or perhaps the Internet). The interface 995c may employ any of a variety of electrically conductive cabling enabling the use of either serial or parallel signal transmission to convey data to the depicted printer 925. Other examples of devices that may be communicatively coupled through one or more interface controllers of the interface 990 include, without limitation, microphones, remote controls, stylus pens, card readers, finger print readers, virtual reality interaction gloves, graphical input tablets, joysticks, other keyboards, retina scanners, the touch input component of touch screens, trackballs, various sensors, a camera or camera array to monitor movement of persons to accept commands and/or data signaled by those persons via gestures and/or facial expressions, sounds, laser printers, inkjet printers, mechanical robots, milling machines, etc.

Where a computing device is communicatively coupled to (or perhaps, actually incorporates) a display (e.g., the depicted example display 980, corresponding to the display 150 and/or 250), such a computing device implementing the processing architecture 2000 may also include the display interface 985. Although more generalized types of interface may be employed in communicatively coupling to a display, the somewhat specialized additional processing often required in visually displaying various forms of content on a display, as well as the somewhat specialized nature of the cabling-based interfaces used, often makes the provision of a distinct display interface desirable. Wired and/or wireless signaling technologies that may be employed by the display interface 985 in a communicative coupling of the display 980 may make use of signaling and/or protocols that conform to any of a variety of industry standards, including without limitation, any of a variety of analog video interfaces, Digital Video Interface (DVI), DisplayPort, etc.

More generally, the various elements of the computing devices described and depicted herein may include various hardware elements, software elements, or a combination of both. Examples of hardware elements may include devices, logic devices, components, processors, microprocessors, circuits, processor components, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), memory units, logic gates, registers, semiconductor device, chips, microchips, chip sets, and so forth. Examples of software elements may include software components, programs, applications, computer programs, application programs, system programs, software development programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. However, determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints, as desired for a given implementation.

Some embodiments may be described using the expression "one embodiment" or "an embodiment" along with their derivatives. These terms mean that a particular feature, structure, or characteristic described in connection with the embodiment is included in at least one embodiment. The appearances of the phrase "in one embodiment" in various places in the specification are not necessarily all referring to the same embodiment. Further, some embodiments may be described using the expression "coupled" and "connected" along with their derivatives. These terms are not necessarily intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other. Furthermore, aspects or elements from different embodiments may be combined.

It is emphasized that the Abstract of the Disclosure is provided to allow a reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment. In the appended claims, the terms "including" and "in which" are used as the plain-English equivalents of the respective terms "comprising" and "wherein," respectively. Moreover, the terms "first," "second," "third," and so forth, are used merely as labels, and are not intended to impose numerical requirements on their objects.

What has been described above includes examples of the disclosed architecture. It is, of course, not possible to describe every conceivable combination of components and/or methodologies, but one of ordinary skill in the art may recognize that many further combinations and permutations are possible. Accordingly, the novel architecture is intended to embrace all such alterations, modifications and variations that fall within the spirit and scope of the appended claims. The detailed disclosure now turns to providing examples that pertain to further embodiments. The examples provided below are not intended to be limiting.

Example 1

An apparatus for a wearable computing device configured to determine depth with respect to another wearable computing device, the apparatus comprising: a first sensor coupled to a first wearable device, the first sensor to generate an indication of a first measured quantity; a sensor output collector to receive the indication of the first measured quantity from the first sensor and to receive an indication of a second measured quantity from a second sensor, the second sensor associated with a second wearable device; and a depth determinator to determine a depth with respect to the second wearable device based on the first measured quantity and the second measured quantity.

Example 2

The apparatus of example 1, the depth determinator to: determine whether the first measured quantity is greater than the second measured quantity; and determine the depth with respect to the second wearable device based on whether the first measured quantity is greater than the second measured quantity.

Example 3

The apparatus of example 1, wherein the first measured quantity and the second measured quantity comprise a temperature, a noise level, a light level, a wireless signal strength, an electrostatic measurement, or a biometric measurement.

Example 4

The apparatus of example 1, the sensor output collector to receive an indication of a third measured quantity from a third sensor, the third sensor associated with a third wearable device, the depth determinator to determine the depth with respect to the second wearable device and the third wearable device based on the first measured quantity, the second measured quantity, and the third measured quantity.

Example 5

The apparatus of example 4, the depth determinator to: determine whether the first measured quantity is greater than the second measured quantity; determine whether the first measured quantity is greater than the third measured quantity; and determine the depth with respect to the second wearable device and the third wearable device based on whether the first measured quantity is greater than the second measured quantity and whether the first measured quantity is greater than the third measured quantity.

Example 6

The apparatus for example 1, the depth determinator to designate one of the first device, the second device, or the third device to use for a wearable device function.

Example 7

The apparatus of example 1, comprising: a fourth sensor coupled to the first wearable device, the fourth sensor to generate an indication of a fourth measured quantity; the sensor output collector to receive the indication of the fourth measured quantity from the fourth sensor and to receive an indication of a fifth measured quantity from a fifth sensor, the fifth sensor associated with the second wearable device; and the depth determinator to validate the depth based on the fourth measured quantity and the fifth measured quantity.

Example 8

The apparatus of example 4, comprising: a fourth sensor coupled to the first wearable device, the fourth sensor to generate an indication of a fourth measured quantity; the sensor output collector to receive the indication of the fourth measured quantity from the fourth sensor, an indication of a fifth measured quantity from a fifth sensor and an indication of a sixth measured quantity from a sixth sensor, the fifth sensor associated with the second wearable device and the sixth sensor associated with the third wearable device; and the depth determinator to validate the depth based on the fourth measured quantity, the fifth measured quantity, and the sixth measured quantity.

Example 9

The apparatus of example 7, wherein the fourth measured quantity and the fifth measured quantity comprise a temperature, a noise level, or a light level, a wireless signal strength, or an electrostatic measurement.

Example 10

The apparatus of any one of examples 1 to 9, wherein the first wearable computing device, the second wearable computing device, and the third wearable computing device comprise removable clothing to be layered.

Example 11

The apparatus of example 10, wherein the first wearable computing device comprises an undergarment, a tee-shirt, a button up shirt, a sweater, or a jacket.

Example 12

The apparatus of example 6, comprising a seventh sensor coupled to the first wearable device, the seventh sensor to generate an indication for the wearable device function.

Example 13

The apparatus of example 1, comprising: an interface coupled to the first wearable device to communicate the depth to a computing device.

Example 14

The apparatus of example 1, comprising: a network interface coupled to the first wearable device to communicate the depth via a network.

Example 15

A method to determine depth for a number of wearable computing devices, the method comprising: receiving an indication of a first measured quantity from a first sensor, the first sensor associated with a first wearable device; receiving an indication of a second measured quantity from a second sensor, the second sensor associated with a second wearable device; and determining a depth for the first wearable device and the second wearable device based on the first measured quantity and the second measured quantity.

Example 16

The method of example 15, comprising: determining whether the first measured quantity is greater than the second measured quantity; and determining the depth based on whether the first measured quantity is greater than the second measured quantity.

Example 17

The method of example 15, wherein the first measured quantity and the second measured quantity comprise a temperature, a noise level, a light level, a wireless signal strength, an electrostatic measurement, or a biometric measurement.

Example 18

The method of example 15, comprising: receiving an indication of a third measured quantity from a third sensor, the third sensor associated with a third wearable device; and determining the depth for the first wearable device, the second wearable device, and the third wearable device based on the first measured quantity, the second measured quantity, and the third measured quantity.

Example 19

The method of example 18, comprising: determining whether the first measured quantity is greater than the second measured quantity; determining whether the first measured quantity is greater than the third measured quantity; and determining the depth based on whether the first measured quantity is greater than the second measured quantity and whether the first measured quantity is greater than the third measured quantity.

Example 20

The method for example 18, comprising designating one of the first device, the second device, or the third device to use for a wearable device function.

Example 21

The method of example 15, comprising: receiving the indication of a fourth measured quantity from a fourth sensor, the fourth sensor associated with the first wearable device; receiving an indication of a fifth measured quantity from a fifth sensor, the fifth sensor associated with the second wearable device; and validating the depth based on the fourth measured quantity and the fifth measured quantity.

Example 22

The method of example 18, comprising: receiving an indication of a fourth measured quantity from a fourth sensor, the fourth sensor associated with the first wearable device; receiving an indication of a fifth measured quantity from a fifth sensor, the fifth sensor associated with the second wearable device; receiving an indication of a sixth measured quantity from a sixth sensor, the sixth sensor associated with the third wearable device; and validating the depth based on the fourth measured quantity, the fifth measured quantity, and the sixth measured quantity.

Example 23

The method of example 22, wherein the fourth measured quantity, the fifth measured quantity, and the sixth measured quantity comprise a temperature, a noise level, or a light level, a wireless signal strength, or an electrostatic measurement.

Example 24

The method of any one of examples 15 to 23, wherein the first wearable computing device, the second wearable computing device, and the third wearable computing device comprise removable clothing to be layered.

Example 25

The method of example 24, wherein the first wearable computing device comprises an undergarment, a tee-shirt, a button up shirt, a sweater, a jacket, or a rain coat.

Example 26

At least one machine readable medium comprising a plurality of instructions that in response to being executed on a wearable device causes the wearable computing device to perform the method of any of examples 15 to 25.

Example 27

An apparatus for a wearable device configured to determine depth of layered wearable devices, the apparatus comprising: a processor; a sensor operably connected to the processor; and a memory comprising a plurality of instructions that in response to being executed by the processor cause the apparatus to determine a depth of the apparatus relative to a number of other wearable devices according to the method of any one of examples 15 to 25.

Example 28

An apparatus for a wearable computing device, the apparatus comprising means for performing the method of any one of examples 15 to 25.

What is claimed is:

1. An apparatus for a wearable computing device configured to determine depth with respect to another wearable computing device, the apparatus comprising:
   a first sensor coupled to a first wearable device, the first sensor to generate an indication of a first measured quantity;
   a sensor output collector to receive the indication of the first measured quantity from the first sensor and to receive an indication of a second measured quantity from a second sensor, the second sensor associated with a second wearable device; and
   a depth determinator to determine a depth with respect to the second wearable device based on the first measured quantity and the second measured quantity.

2. The apparatus of claim 1, the depth determinator to:
   determine whether the first measured quantity is greater than the second measured quantity; and
   determine the depth with respect to the second wearable device based on whether the first measured quantity is greater than the second measured quantity.

3. The apparatus of claim 1, wherein the first measured quantity and the second measured quantity comprise a temperature, a noise level, a light level, a wireless signal strength, an electrostatic measurement, or a biometric measurement.

4. The apparatus of claim 1, the sensor output collector to receive an indication of a third measured quantity from a third sensor, the third sensor associated with a third wearable device, the depth determinator to determine the depth with respect to the second wearable device and the third wearable device based on the first measured quantity, the second measured quantity, and the third measured quantity.

5. The apparatus of claim 4, the depth determinator to:
determine whether the first measured quantity is greater than the second measured quantity;
determine whether the first measured quantity is greater than the third measured quantity; and
determine the depth with respect to the second wearable device and the third wearable device based on whether the first measured quantity is greater than the second measured quantity and whether the first measured quantity is greater than the third measured quantity.

6. The apparatus of claim 4, comprising:
a fourth sensor coupled to the first wearable device, the fourth sensor to generate an indication of a fourth measured quantity;
the sensor output collector to receive the indication of the fourth measured quantity from the fourth sensor, an indication of a fifth measured quantity from a fifth sensor and an indication of a sixth measured quantity from a sixth sensor, the fifth sensor associated with the second wearable device and the sixth sensor associated with the third wearable device; and
the depth determinator to validate the depth based on the fourth measured quantity, the fifth measured quantity, and the sixth measured quantity.

7. The apparatus for claim 1, the depth determinator to designate one of the first device, the second device, or the third device to use for a wearable device function.

8. The apparatus of claim 7, comprising a seventh sensor coupled to the first wearable device, the seventh sensor to generate an indication for the wearable device function.

9. The apparatus of claim 1, comprising:
a fourth sensor coupled to the first wearable device, the fourth sensor to generate an indication of a fourth measured quantity;
the sensor output collector to receive the indication of the fourth measured quantity from the fourth sensor and to receive an indication of a fifth measured quantity from a fifth sensor, the fifth sensor associated with the second wearable device; and
the depth determinator to validate the depth based on the fourth measured quantity and the fifth measured quantity.

10. The apparatus of claim 9, wherein the fourth measured quantity and the fifth measured quantity comprise a temperature, a noise level, or a light level, a wireless signal strength, or an electrostatic measurement.

11. The apparatus of claim 1, wherein the first wearable computing device, the second wearable computing device, and the third wearable computing device comprise removable clothing to be layered.

12. The apparatus of claim 11, wherein the first wearable computing device comprises an undergarment, a tee-shirt, a button up shirt, a sweater, or a jacket.

13. The apparatus of claim 1, comprising:
an interface coupled to the first wearable device to communicate the depth to computing device.

14. A method to determine depth for a number of wearable computing devices, the method comprising:
receiving an indication of a first measured quantity from a first sensor, the first sensor associated with a first wearable device;
receiving an indication of a second measured quantity from a second sensor, the second sensor associated with a second wearable device; and
determining a depth for the first wearable device and the second wearable device based on the first measured quantity and the second measured quantity.

15. The method of claim 14, comprising:
determining whether the first measured quantity is greater than the second measured quantity; and
determining the depth based on whether the first measured quantity is greater than the second measured quantity.

16. The method of claim 14, wherein the first measured quantity and the second measured quantity comprise a temperature, a noise level, a light level, a wireless signal strength, an electrostatic measurement, or a biometric measurement.

17. The method of claim 14, comprising:
receiving an indication of a third measured quantity from a third sensor, the third sensor associated with a third wearable device; and
determining the depth for the first wearable device, the second wearable device, and the third wearable device based on the first measured quantity, the second measured quantity, and the third measured quantity.

18. The method of claim 17, comprising:
determining whether the first measured quantity is greater than the second measured quantity;
determining whether the first measured quantity is greater than the third measured quantity; and
determining the depth based on whether the first measured quantity is greater than the second measured quantity and whether the first measured quantity is greater than the third measured quantity.

19. The method for claim 17, comprising designating one of the first device, the second device, or the third device to use for a wearable device function.

20. The method of claim 17, comprising:
receiving an indication of a fourth measured quantity from a fourth sensor, the fourth sensor associated with the first wearable device;
receiving an indication of a fifth measured quantity from a fifth sensor, the fifth sensor associated with the second wearable device;
receiving an indication of a sixth measured quantity from a sixth sensor, the sixth sensor associated with the third wearable device; and
validating the depth based on the fourth measured quantity, the fifth measured quantity, and the sixth measured quantity.

21. The method of claim 14, comprising:
receiving the indication of a fourth measured quantity from a fourth sensor, the fourth sensor associated with the first wearable device
receiving an indication of a fifth measured quantity from a fifth sensor, the fifth sensor associated with the second wearable device; and
validating the depth based on the fourth measured quantity and the fifth measured quantity.

* * * * *